United States Patent [19]

Ninomiya et al.

[11] Patent Number: 5,840,994
[45] Date of Patent: Nov. 24, 1998

[54] PROCESS FOR PRODUCING DITRIMETHYLOLPROPANE

[75] Inventors: Teruyuki Ninomiya; Toshio Watanabe; Takaki Ikebe; Atsushi Iwamoto, all of Okayama-ken, Japan

[73] Assignee: Mitsubishi Gas Chemical Company, Inc., Tokyo, Japan

[21] Appl. No.: 820,080

[22] Filed: Mar. 19, 1997

[30] Foreign Application Priority Data

Apr. 3, 1996 [JP] Japan .................................. 8-081363

[51] Int. Cl.⁶ .................................................. C07C 41/00
[52] U.S. Cl. ............................................................. 568/580
[58] Field of Search ............................................. 568/580

[56] References Cited

U.S. PATENT DOCUMENTS 3,829,507  8/1974  Zey ........................................ 568/680
3,962,347  6/1976  Herz ..................................... 360/615 R
5,324,863  6/1994  Sjogreen et al. ..................... 568/680

OTHER PUBLICATIONS

Mank et al, Chemical abstract vol 115 No. 114021, Process for recording & conversing of L. ethylanolen to trimethylolpropone (1991).

Primary Examiner—John Kight
Assistant Examiner—Raymond Covington
Attorney, Agent, or Firm—Frishauf, Holtz, Goodman, Langer & Chick, P.C.

[57] ABSTRACT

A process for producing ditrimethylolpropane which comprises reacting trimethylolpropane, 2-ethylacrolein, and formaldehyde in the presence of a basic catalyst.

Ditrimethylolpropane is produced efficiently and industrially advantageously.

20 Claims, No Drawings

PROCESS FOR PRODUCING DITRIMETHYLOLPROPANE

FIELD OF THE INVENTION

The present invention relates to a process for producing ditrimethylolpropane (hereinafter referred to as DITMP) which is useful as a material for polyacrylates, polyether polyols, polyurethanes, alkyd resins, and synthetic lubricants.

PRIOR ART OF THE INVENTION

DITMP is generally obtained as a byproduct in the production of trimethylolpropane (hereinafter referred to as TMP). TMP is produced by the aldol reaction followed by the Cannizzaro reaction of formaldehyde and normal-butyraldehyde in the presence of a basic catalyst. TMP is separated and purified by distillation in the last step of the process. DITMP is contained in the residue formed by the distillation in this step In conventional processes, DITMP is obtained from this residue by recrystallization. The conventional processes are described, for example, in Japanese Patent Application Laid-Open No. Showa 47(1972)-30611 (USP 3,829,507) and Japanese Patent Application Laid-Open No. Showa 49(1974)-133311 (USP 3,962,347). Processes for increasing the amount of DITMP formed as a byproduct by conducting the reaction for producing TMP under a specific condition are described, for example, in Japanese Patent Application Laid-Open No. Showa 57(1982)-139028 and Japanese Patent Application Laid-Open No. Showa 57(1982)-142929.

On the other hand, as the process for obtaining DITMP itself by synthesis, a process in which DITMP is obtained by forming the ether bond by condensation with dehydration of two molecules of TMP has been known. As the catalyst for the condensation with dehydration, an acid catalyst is advantageously used. Synthesis of DITMP by this process and by a partially modified process of this process is described, for example, in Japanese Patent Application (as a national phase under PCT) Laid-Open No. Heisei 6(1994)-501470 (USP 5,324,863).

The above process of obtaining DITMP as a byproduct in the production of TMP has the following problems.

In the most popular process for producing DITMP, DITMP is separated from the residue formed by distillation of TMP. DITMP must be efficiently separated from miscellaneous products which are formed from materials for producing TMP, such as formaldehyde and normal-butyraldehyde, during the reaction for synthesis of TMP and during distillation to separate TMP. DITMP must be separated also from byproducts other than DITMP, such as acetals formed from TMP and formaldehyde. Therefore, the process for the separation becomes inevitably complicated. Because of the complicated process, the amount of DITMP separated from the residue of distillation remains less than 70%.

An increase in the amount of DITMP formed as a byproduct during the production of TMP has been attempted by conducting the reaction for producing TMP under a specific condition. However, the yield of DITMP by the attempted process is about 20% by mol based on the amount of normal-butyraldehyde, and this yield is only 2 to 3 times as much as that by the conventional processes.

Under the above circumstances, the amount of production of DITMP is inevitably restricted by the amount of production of TMP because DITMP is a byproduct in the production of TMP. Therefore, the supply of DITMP is considered to be behind the demand which is increasing.

On the other hand, the process for producing DITMP by forming the ether bond by condensation with dehydration of two molecules of TMP can solve the problem on the supply of DITMP.

However, because one molecule of TMP has three reactive alcoholic hydroxyl groups, and the reaction takes place between molecules of TMP, formation of ethers which are condensation products of 3 or more molecules of TMP inevitably takes place. To suppress the formation of such ethers, the conversion in the condensation with dehydration of TMP must be suppressed to a low value, and this causes a large economic disadvantage in view of the recovery of the unreacted TMP.

For improving the above drawback, in a process described in the above-mentioned Patent Application Laid-Open No. Heisei 6(1994)-501470, some of the three alcoholic hydroxyl groups in TMP are converted to esters by reaction with lower fatty acids in advance, and the obtained modified TMP is used as the material. However, in the above process, it is not possible that just two alcoholic hydroxyl groups in the same molecule of TMP are selectively converted into esters of lower fatty acids by the reaction in advance. Therefore, this process does not provide any essential solution to the above problem. This process has another drawback in that the modified TMP in which one or two alcoholic hydroxyl groups have been converted into esters produces a modified DITMP having the alcoholic hydroxyl groups in the form of the esters, and an additional process is necessary to regenerate DITMP from the modified DITMP by hydrolysis. This causes an additional economical disadvantage.

SUMMARY OF THE INVENTION

Accordingly, the present invention has the object of providing a process for producing DITMP efficiently and industrially advantageously.

As the results of extensive studies by the present inventors to develop the process for producing DITMP which can solve the above problems, it was discovered that DITMP can efficiently be produced by reacting TMP, 2-ethylacrolein, and formaldehyde in the presence of a basic catalyst. The present invention has been completed on the basis of the discovery.

The present invention provides a process for producing ditrimethylolpropane which comprises reacting trimethylolpropane, 2-ethylacrolein, and formaldehyde in the presence of a basic catalyst.

DETAILED DESCRIPTION OF THE INVENTION

The present invention is described in more detail in the following.

The reaction of the present invention can be shown as following:

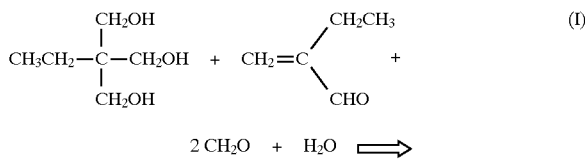

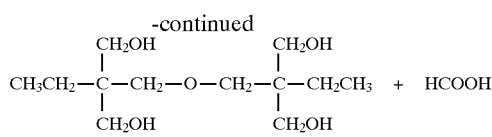

Formic acid produced by the reaction becomes a formate by the reaction with the basic catalyst.

In the process of the present invention, the presence of the basic catalyst is important in the reaction of TMP, 2-ethylacrolein, and formaldehyde. The use of the basic catalyst enables suppressing the formation of ethers which are condensation products of 3 or more molecules of TMP and inevitably formed in the conventional processes.

Examples of the basic catalyst used in the present invention include hydroxides and carbonates of alkali metals and alkaline earth metals, such as sodium hydroxide, potassium hydroxide, calcium hydroxide, lithium hydroxide, sodium carbonate, potassium carbonate, calcium carbonate, and lithium carbonate; and organic basic compounds, particularly tertiary amines, such as trimethylamine, triethylamine, diethylmethylamine, dimethylethylamine, triisopropylamine, and tributylamine.

Among the above basic catalysts, aliphatic amines are particularly preferably used because DITMP can be obtained with a high yield and also because no ashes are left remaining in the product, and DITMP of a high quality is obtained.

The amount of the basic catalyst used in the process is 1.0 to 2.0 mol, preferably 1.1 to 1.3 mol, per 1 mol of 2-ethylacrolein used in the reaction.

As TMP used as a starting material in the process of the present invention, TMP conventionally available as an industrial product can be used without additional purification. Formaldehyde used as another starting material is not particularly limited with respect to the form as long as formaldehyde is prepared in accordance with the ordinary industrial standards. A form which is most suitable for the actually conducted process can be selected. For example, an aqueous formalin solution having a concentration in accordance with the industrial standard or a solid paraformaldehyde can be used.

The amount of TMP used in the process is in the range of 1.0 to 10 mol, preferably in the range of 3.0 to 5.0 mol, per 1 mol of 2-ethylacrolein used in the reaction. When the amount of TMP is in large excess relative to the amount of 2-ethylacrolein, the yield of DITMP based on the amount of 2-ethylacrolein is increased. However, an excess amount of TMP is not preferable in view of the recovery of the unreacted TMP. The amount of formaldehyde used in the process is in the range of 2.0 to 5.0 mol, preferably in the range of 2.1 to 2.3 mol, per 1 mol of 2-ethylacrolein used in the reaction. When one or both of the amounts of TMP and formaldehyde are less than the above respective ranges, the formed amount of TMP is decreased, and the amount of impurities formed by side reactions is increased. Therefore, the separation of DITMP becomes economically disadvantageous. When the amount formaldehyde is more than the above range, a larger amount of unreacted formaldehyde must be recovered, and the amount of byproducts, such as acetals formed from formaldehyde and TMP, is increased. Therefore, the separation of DITMP becomes economically disadvantageous.

In the process of the present invention, the reaction can be conducted in a half-melt condition by heating the reaction mixture to a temperature above the melting point of TMP without using any solvent except for water contained in the aqueous formalin solution. However, a solvent may also be used where necessary. Examples of the preferable solvent include water and aliphatic ethers, such as dioxane, tetrahydrofuran, diethyl ether, diglyme, and tetraglyme. A single type or a mixture of two or more types of the solvent can be used.

In the process of the present invention, the reaction temperature can be adjusted in a range suitable for the reaction which depends on the type of the catalyst. For example, the reaction temperature is adjusted in the range of 40° to 60° C. when sodium hydroxide or potassium hydroxide is used, and in the range of 80° to 120° C. when an aliphatic amine, such as triethylamine, is used. In general, when the reaction temperature is 10° C. or lower, the rate of the reaction is very low, and the condition is not practical. When the reaction temperature is higher than 120° C., side reactions become significant to cause decrease in the yield of DITMP and troubles in separation and purification of DITMP.

When the reaction temperature is adjusted to 90° to 100° C. or higher, the pressure inside the reaction system can be kept at an atmospheric pressure or higher, generally at 1 to 5 kg/cm$^2$, in order to maintain the prescribed reaction temperature. The pressure may be added by using an inert gas, such as nitrogen or argon, if necessary.

The reaction time is varied depending on the reaction temperature and the type of the catalyst. The reaction time is set generally in the range of 0.5 to 6 hours, preferably in the range of 1.0 to 3.0 hours.

In the process of the present invention, the unreacted starting materials having lower boiling points and byproducts are removed from the reaction product by successive distillations after the reaction is finished, and DITMP which is the object compound of the process can be obtained as crystal by recrystallization of the obtained reaction product from water.

To summarize the advantages obtained by the present invention, DITMP can efficiently be produced from TMP, 2-ethylacrolein, and formaldehyde. In accordance with the process of the present invention, the unreacted starting materials having lower boiling points can be recovered from the reaction product by distillation and used again by recycling, and byproducts can also be removed easily by distillation. Thus, the process of the present invention is excellent as the industrial process.

The present invention is described in more detail with reference to examples in the following. However, the present invention is not limited by the examples.

EXAMPLE 1

In a 1 liter glass pressure-resistant reactor equipped with a stirrer, 402.0 g (3.00 mol) of TMP, 165.0 g (corresponding to 2.20 mol of formaldehyde) of a 40% aqueous solution of formaldehyde, 84.0 g (1.00 mol) of 2-ethylacrolein, and 111.1 g (1.10 mol) of triethylamine were mixed together, and the reaction was allowed to proceed at 90° C. for 2 hours in the resultant mixture. The obtained reaction solution was analyzed by gas chromatography, and 116.8 g (0.47 mol) of DITMP was found to be formed. This corresponds to the yield of 46.7% by mol based on the amount of 2-ethylacrolein used as the starting material.

EXAMPLE 2

In a 3 liter glass reactor equipped with a stirrer, 268.0 g (2.00 mol) of TMP, 1500.0 g of water, and 165.0 g (2.20 mol) of a 40% aqueous solution of formaldehyde were mixed together. To the obtained solution, 84.0 g (1.00 mol) of 2-ethylacrolein and 96.0 g (corresponding to 1.20 mol of sodium hydroxide) of a 50% aqueous solution of sodium hydroxide were added dropwise during 30 minutes. After the addition was finished, the resultant solution was heated to 60° C., and the reaction was allowed to proceed for additional 30 minutes. The obtained reaction solution was analyzed by gas chromatography, and 88.0 g (0.35 mol) of DITMP was found to be formed. This corresponds to the yield of 35.2% by mol based on the amount of 2-ethylacrolein used as the starting material.

EXAMPLE 3

The reaction was conducted in accordance with the same procedures as those conducted in Examples 1 except that TMP was used in an amount of 670.0 g (5.00 mol). The obtained reaction solution was analyzed by gas chromatography, and 171.5 g (0.69 mol) of DITMP was found to be formed. This corresponds to the yield of 68.6% by mol based on the amount of 2-ethylacrolein used as the starting material.

COMPARATIVE EXAMPLE 1

In a flask equipped with a stirrer, 1340.0 g (10.00 mol) of TMP and 1.0 g of sulfuric acid were mixed together, and the resultant mixture was heated to 165° C. under a pressure of 5 mmHg. After 4 hours of the reaction, the obtained reaction solution was analyzed by gas chromatography and found to contain 90.0 g (0.36 mol) of DITMP and 1051.3 g (7.85 mol) of unreacted TMP. This corresponds to the conversion of 21.5% by mol, the selectivity of 33.5% by mol, and the yield of 7.2% by mol based on the amount of TMP used as the starting material.

COMPARATIVE EXAMPLE 2

In accordance with the same procedures as those conducted in Examples 1, 268.0 g (2.00 mol) of TMP and 202.0 g (2.00 mol) of triethylamine were reacted. The obtained reaction solution was analyzed by gas chromatography and found to contain 0.0 g of DITMP and 267.1 g (1.99 mol) of unreacted TMP. This means that 99.7% by mol of TMP used as the starting material was recovered as unreacted TMP.

What is claimed is:

1. A process for producing ditrimethylolpropane which comprises reacting trimethylolpropane, 2-ethylacrolein, and formaldehyde in the presence of a basic catalyst, wherein the basic catalyst is an aliphatic amine.

2. A process according to claim 1 wherein the aliphatic amine is a tertiary amine.

3. A process according to claim 1 wherein the amount of the basic catalyst is in the range of 1.0 to 2.0 mol per 1 mol of the 2-ethylacrolein.

4. A process according to claim 1 wherein the amount of the basic catalyst is in the range of 1.1 to 1.3 mol per 1 mol of the 2-ethylacrolein.

5. A process for producing ditrimethylolpropane which comprises reacting trimethylolpropane, 2-ethylacrolein, and formaldehyde in the presence of a basic catalyst, wherein the amount of the trimethylolpropane is in the range of 1.0 to 10.0 mol per 1 mol of the 2-ethylacrolein.

6. A process according to claim 1 wherein the amount of formaldehyde is in the range of 2.0 to 5.0 mol per 1 mol of 2-ethylacrolein.

7. A process according to claim 2 wherein the tertiary amine is selected from the group consisting of trimethylamine, triethylamine, diethylmethylamine, dimethylethylamine, triisopropylamine and tributylamine.

8. A process according to claim 7 wherein the process is carried out at a temperature of 80° to 120° C. and for a reaction time of 0.5 to 6 hours.

9. A process according to claim 7 wherein the process is carried out at a temperature of 90° to 100° C. at a pressure of 1 to 5 kg/cm$^2$ and for a reaction time of 1 to 3 hours.

10. A process according to claim 8 wherein the amount of the basic catalyst is 1.0 to 2.0 mol per 1 mol of the 2-ethylacrolein.

11. A process according to claim 9 wherein the amount of formaldehyde is 2.0 to 5.0 mol per 1 mol of the 2-ethylacrolein.

12. A process according to claim 5 wherein the amount of the basic catalyst is 1.0 to 2.0 mol per 1 mol of the 2-ethylacrolein.

13. A process according to claim 5 wherein the amount of the basic catalyst is 1.1 to 1.3 mol per 1 mol of the 2-ethylacrolein.

14. A process according to claim 13 wherein the amount of the trimethylolpropane is 3.0 to 5.0 mol per 1 mol of the 2-ethylacrolein.

15. A process according to claim 14 wherein the amount of the formaldehyde is 2.0 to 5.0 mol per 1 mol of the 2-ethylacrolein.

16. A process according to claim 15 wherein the basic catalyst is a hydroxide or carbonate of an alkali metal or an alkaline earth metal.

17. A process according to claim 15 wherein the basic catalyst is selected from the group consisting of sodium hydroxide, potassium hydroxide, calcium hydroxide, lithium hydroxide, sodium carbonate, potassium carbonate, calcium carbonate and lithium carbonate.

18. A process according to claim 17 wherein the basic catalyst is sodium hydroxide or potassium hydroxide, and the process is carried out at a temperature of 80° to 120° C.

19. A process according to claim 18 wherein the process is carried out at a reaction time of 0.5 to 6 hours.

20. A process according to claim 5 wherein the basic catalyst is an aliphatic amine.

* * * * *